United States Patent [19]

Hayes et al.

[11] Patent Number: 4,507,296

[45] Date of Patent: Mar. 26, 1985

[54] TETRAZOLES, PHARMACEUTICAL USE AND COMPOSITIONS

[75] Inventors: Roger Hayes; David E. Bays; John W. M. Mackinnon; Linda Carey, all of Hertfordshire, England

[73] Assignee: Glaxo Group Limited, London, England

[21] Appl. No.: 569,152

[22] Filed: Jan. 9, 1984

Related U.S. Application Data

[63] Continuation of Ser. No. 401,396, Jul. 23, 1982.

[30] Foreign Application Priority Data

Feb. 16, 1982 [GB] United Kingdom ................. 8204483

[51] Int. Cl.³ .................... A61K 31/41; C07D 257/06; C07D 257/04
[52] U.S. Cl. .................................... 514/212; 514/236; 514/237; 514/326; 514/340; 514/381; 514/382
[58] Field of Search ................ 544/132; 546/210, 276; 548/193, 214, 251; 424/246.56, 263, 267, 269, 270

[56] References Cited

U.S. PATENT DOCUMENTS

4,318,913  3/1982  Clitherow et al. ................. 546/210

OTHER PUBLICATIONS

Chemical Abstracts, vol. 99 (1983), Item 175,769(d) Abstracting Japan Kokai Tokkyo Koho JP 58 90,569 [83 90,569], May 30, 1983, [(Priority Great Britain Appl. 81/34,871), (Filed Nov. 19, 1981)]; 12 pages.

*Primary Examiner*—Robert T. Bond
*Attorney, Agent, or Firm*—Bacon & Thomas

[57] ABSTRACT

The invention relates to compounds of the general formula (I)

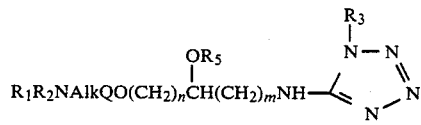

and physiologically acceptable salts or hydrates thereof, in which the substituents are defined later in the specification.

The compounds show pharmacological activity as selective histamine $H_2$-antagonists.

7 Claims, No Drawings

TETRAZOLES, PHARMACEUTICAL USE AND COMPOSITIONS

This application is a continuation of application Ser. No. 401,396, filed July 23, 1982.

This invention relates to novel heterocyclic derivatives having action on histamine receptors, to processes for the preparation thereof, to pharmaceutical compositions containing them and to their use in therapeutics.

Certain novel heterocyclic derivatives have now been found which have potent activity as $H_2$-antagonists. These compounds, which are more particularly described below, for example show inhibition of the secretion of gastric acid when this is stimulated via histamine receptors (Ash and Schild, Brit. J. Pharmacol. Chemother, 1966, 27, 427). Their ability to do so can be demonstrated in the perfused rat stomach using the method described in British Patent Specification No. 1565966, modified by the use of sodium pentobarbitone (50 mg/kg) as anaesthetic instead of urethane, and in conscious dogs equipped with Heidenhain pouches using the method described by Black et al., Nature 1972 236, 385. Furthermore, the compounds antagonise the effect of histamine on the contraction frequency of isolated guinea pig right atrium.

Compounds with histamine $H_2$-blocking activity may be used in the treatment of conditions where there is an advantage in lowering gastric acidity, particularly in gastric and peptic ulceration, as a prophylactic measure in surgical procedures, and in the treatment of allergic and inflammatory conditions where histamine is a known mediator, Thus they may be used for example, either alone or in a combination with other active ingredients in the treatment of allergic and inflammatory conditions of the skin.

The present invention provides compounds of the general formula (1).

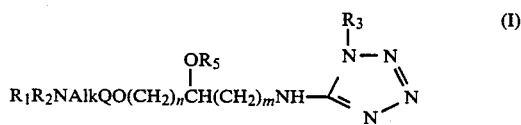

and physiologically acceptable salts, hydrates and bioprecursors thereof, in which $R_1$ represents hydrogen, $C_{1-14}$ alkyl, cycloalkyl, alkenyl, alkynyl, aralkyl, trifluoroalkyl, heteroaralkyl or alkyl substituted by cycloalkyl, hydroxy, alkoxy, amino, alkylamino or dialkylamino; and $R_2$ represents hydrogen or $C_{1-4}$ alkyl group; or $R_1$ and $R_2$ together with the nitrogen atom to which they are attached form a 5 to 10 membered ring which may be saturated or may contain at least one double bond, may be unsubstituted or may be substituted by one or more $C_{1-3}$ alkyl groups, e.g. methyl, or a hydroxy group and/or may contain another heteroatom selected from oxygen or sulphur;

Alk represents a straight or branched alkylene chain of 1 to 3 carbon atoms;

Q represents a benzene ring in which incorporation into the rest of the molecule is through bonds at the 1- and 3- or 1- and 4-positions;

$R_5$ represents hydrogen or acyl;

n and m, which may be the same or different, are each 1 or 2; and $R_3$ represents hydrogen, alkyl, alkenyl, aralkyl, hydroxy $C_{2-6}$ alkyl, alkoxy $C_{2-6}$ alkyl or $C_{1-4}$ alkanoyloxy-$C_{2-6}$ alkyl.

The term "alkyl" as a group or part of a group means that the group is straight or branched, and unless otherwise stated, has preferably 1 to 6 carbon atoms and in particular 1 to 4 carbon atoms, e.g. methyl or ethyl; and the terms "alkenyl" and "alkynyl" mean that the groups preferably contain 3 to 6 carbon atoms. The term "cycloalkyl" means that the group has 3 to 8 carbon atoms. The term "aryl" as a part of a group preferably means phenyl or substituted phenyl, for example phenyl substituted with one or more $C_{1-3}$ alkyl or alkoxy groups or halogen atoms, e.g. fluorine. The term acyl or the acyl portion of an acyloxyalkyl group means an aroyl, aralkanoyl or $C_{1-6}$ alkanoyl group. Examples of acyloxyalkyl groups include acetoxymethyl, formyloxymethyl, benzoyloxymethyl and phenylacetoxymethyl. The term heteroaryl as a part of a group means a 5 or 6 membered monocyclic ring containing from 1 to 3 heteroatoms selected from oxygen, nitrogen and sulphur, e.g. thienyl, pyrrolyl, pyridyl, furyl or thiazolyl. The heteroaryl ring may be unsubstituted or substituted by $C_{1-3}$ alkyl, $C_{1-3}$ alkoxy, hydroxyalkyl, aminoalkyl, alkylaminoalkyl, dialkylaminoalkyl or halogen, for example, the heteroaryl ring may be thienyl or furyl substituted by $C_{1-3}$ alkyl, aminoalkyl, alkylaminoalkyl, dialkylaminoalkyl or hydroxyalkyl, pyrrolyl substituted by $C_{1-3}$ alkyl, pyridyl substituted by $C_{1-3}$ alkyl, $C_{1-3}$ alkoxy, halogen or hydroxyalkyl or thiazolyl substituted by $C_{1-3}$ alkyl or hydroxyalkyl. The alkyl portion of a heteroaralkyl group is a straight or branched $C_{1-4}$ alkyl chain, and the heteroaryl ring is linked to the alkyl portion through a carbon atom.

According to one aspect the invention provides compounds of formula (I) in which $R_5$ represents hydrogen or a $C_{1-4}$ alkanoyl group and $R_1$, $R_2$, $R_3$, Alk, Q, m and n are as defined in formula (I).

Preferred compounds of formula (I) are those in which $R_1$ represents $C_{1-8}$ alkyl (e.g. methyl, propyl, butyl or heptyl), $C_{1-4}$ alkyl substituted by a trifluoromethyl group (e.g. 2,2,2-trifluoroethyl), $C_{2-4}$ alkyl substituted by hydroxy or a di $C_{1-3}$ alkylamino group (e.g. 3-hydroxypropyl or dimethylaminoethyl), $C_{5-7}$ cycloalkyl (e.g. cyclohexyl), $C_{3-5}$ alkenyl (e.g. allyl), phenyl $C_{1-3}$ alkyl (e.g. benzyl), or a heteroaryl $C_{1-3}$ alkyl group where the heteroaryl ring contains one heteroatom (e.g. 2-furylmethyl);

$R_2$ represents hydrogen or methyl; or $R_1R_2N$ represents a 5 to 7 membered ring optionally containing a double bond, an oxygen atom or an alkyl (e.g. methyl) substituent (e.g. piperidino, morpholino, 4-methylpiperidino, pyrrolidino, hexamethyleneimino or tetrahydropyridino);

Alk represents methylene;

$R_3$ represents hydrogen, alkyl (e.g. methyl or ethyl), hydroxy $C_{2-4}$ alkyl (e.g. hydroxyethyl);

Q represents a benzene ring incorporated into the rest of the molecule through bonds at the 1- and 3-positions;

$R_5$ represents hydrogen or alkanoyl (e.g. acetyl); and n and m both represent 1 or one of n and m represents 2.

A further preferred class of compounds of formula (I) are those of formula (II)

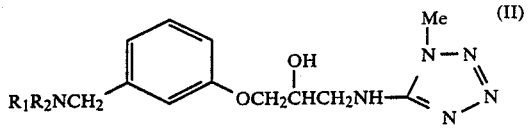

in which $R_1R_2N$ is dimethylamino, pyrrolidino, piperidino or hexamethylenimino, more preferably piperidino.

A particularly preferred compound is 1-[(1-methyl-1H-tetrazol-5-yl)amino]-3-[3-(1-piperidinylmethyl)-phenoxy]-2-propanol;

and physiologically acceptable salts thereof.

The invention includes the compounds of formula (I) in the form of physiologically acceptable salts with inorganic and organic acids. Particularly useful salts include hydrochlorides, hydrobromides, sulphates, methanesulphonates, acetates, maleates, succinates, citrates, tartrates, fumarates and benzoates. The compounds of formula (I) and their salts may also form hydrates, which hydrates are also to be considered as part of the invention. The compounds of formula (I) can exhibit tautomerism and the formula is intended to cover all tautomers. Where optical isomers may exist the formula is intended to cover all diastereoisomers and optical enantiomers. The term bioprecursors as used herein means compounds which have a structure different to that of the compounds of formula (I) but which, upon administration to the animal or human being are converted in the body into a compound of formula (I).

The compounds according to the invention, preferably in the form of a salt may be formulated for administration in any convenient way and the invention includes within its scope pharmaceutical compositions containing at least one compound according to the invention adapted for use in human or veterinary medicine. Such compositions may be formulated in a conventional manner using one or more pharmaceutically acceptable carriers or excipients. Such compositions may also contain if required other active ingredients, e.g. $H_1$-antagonists.

Thus the compounds according to the invention may be formulated for oral, buccal, topical, parenteral, or rectal administration. Oral administration is preferred.

For oral administration, the pharmaceutical compositions may take the form of for example, tablets, capsules, powders, solutions, syrups or suspensions prepared by conventional means with acceptable excipients. For buccal administration the composition may take the form of tablets or lozenges formulated in conventional manner.

The compounds of the invention may be formulated for parenteral administration by bolus injection or continuous infusion. Formulations for injection may be presented in unit dosage form in ampoules, or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for reconstitution with a suitable vehicle, e.g. sterile pyrogen-free water before use.

The compound of the invention may also be formulated in rectal compositions such as suppositories or retention enemas, e.g. containing conventional suppository bases such as cocoa butter or other glyceride.

For topical application, the compounds of the invention may be formulated as ointments, creams, gels, lotions, powders or sprays in a conventional manner.

For internal administration a convenient daily dosage regime of the compounds according to the invention would be 1 to 4 doses to the total of some 5 mg to 1.5 g per day, preferably 5 to 500 mg per day dependent upon the condition of the patient.

It will be appreciated that in the methods of the preparation of compounds of formula (I) given below, for certain reaction steps it may be necessary to protect various reactive substituents in the starting materials for a particular reaction and subsequently to remove the protecting group. Such protection and subsequent deprotection may be particularly pertinent where $R_1$ and/or $R_2$ in intermediates used to prepare compounds of formula (I) are hydrogen atoms and/or when $R_3$ in intermediates is an alkyl group bearing a hydroxy substituent and/or when $R_5$ in intermediates is a hydrogen atom. Standard protection and deprotection procedures can be employed. For example an amino group may be protected by formation of a phthalimide which may subsequently be cleaved by treatment with a hydrazine, e.g. hydrazine hydrate or a primary amine, for example methylamine; or by formation of a benzyl derivative which may subsequently be cleaved by hydrogenolysis in the presence of a catalyst e.g. palladium. When $R_3$ is hydrogen, this may be protected by formation of a N-alkoxyalkyl (e.g. ethoxymethyl) derivative which may subsequently be cleaved by treatment with dilute acid. The hydroxyl group $OR_5$ where $R_5$ is hydrogen may be protected, for example as an acyloxy group or as an ether group such as trialkylsilyl e.g. trimethylsilyl, aralkyl such as benzyl, benzhydryl or trityl, tetrahydropyranyl or alkoxymethyl, e.g. methoxymethyl ethers. Such protecting groups may be removed by conventional procedures of JFW McOmie. For example, benzyl and benzhydryl ether groups may be removed by catalytic hydrogenolysis with for example hydrogen and a palladium catalyst, and trityl, tetrahydropyranyl, alkoxymethyl and trialkylsilyl ether groups may be removed by acid hydrolysis.

In describing the processes which may be used for preparing the compounds of formula (I) or intermediates useful in the preparation thereof, any of $R_1$ to $R_3$, $R_5$, Alk, Q, n and m are as defined in formula (I) unless otherwise stated.

Compounds of formula (I) in which $R_5$ is hydrogen may be prepared by heating the diamine (III)

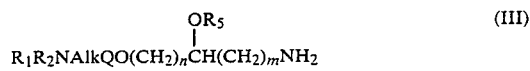

in which $R_5$ represents hydrogen with a compound of formula (IV)

in which $R_3'$ is the group $R_3$ or a group convertible thereto, and

P is a leaving group such as halogen e.g. bromine.

The reaction may be carried out in the absence or presence of a solvent such as acetonitrile, water or an alcohol (e.g. ethanol) at for example 80°–150° C., and optionally in a sealed vessel.

Compounds of formula (IV) are either known compounds or may be prepared by methods analogous to those described in British Patent Specification No. 1364917 and G. B. Barlin, J. Chem. Soc. (B) 1967, 641.

Compounds of formula (I) in which $R_5$ is acyl may be prepared by treating the corresponding compound of formula (I) in which $R_5$ represents hydrogen with either an appropriate acid or an activated derivative thereof (e.g. an acid anhydride or acid chloride). The reaction may be carried out at room temperature optionally in the presence of a solvent (e.g. pyridine, tetrahydrofuran, acetone or dimethylformamide), and preferably in the presence of a base (e.g. pyridine, triethylamine or an alkali metal carbonate such as potassium carbonate).

Compounds of formula (I) in which Alk is $CH_2$ and $R_5$ is hydrogen may also be prepared by treating an aldehyde of formula (V)

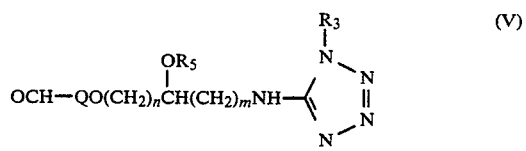
(V)

with an amine $R_1R_2NH$ in a solvent such as tetrahydrofuran or an alkanol, e.g. methanol, followed by reduction using for example a hydride reducing agent such as an alkali or alkaline earth metal borohydride, e.g. sodium borohydride or lithium aluminium hydride, or hydrogen and a metal catalyst such as palladium or platinum. The reactions may be carried out at a temperature of 0° to 30° C.

The intermediates of formula (V) may be prepared from compounds of formula (VI)

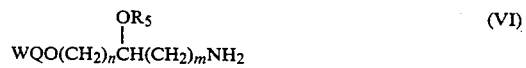
(VI)

in which W represents a protected aldehyde group, e.g. a cyclic acetal such as an ethylene acetal, by methods analogous to those described herein for preparing compounds of formula (I) from the amine of formula (III).

In the above discussion of the processes available for the production of compounds according to the invention reference has been made to the primary amines of formula (III). These amines are novel compounds and may be made by a number of processes which are described below.

Diamines of formula (III) in which $R_5$ is hydrogen and n is 1 may be prepared by reacting a compound of formula (VII)

(VII)

with an epoxide of formula (VIII)

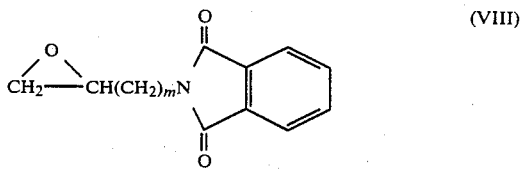
(VIII)

to produce a diamine of formula (IX)

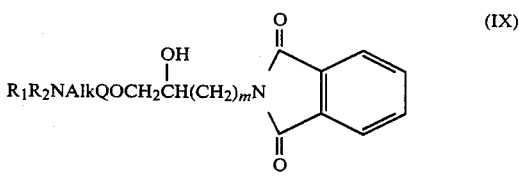
(IX)

The reaction may be carried out in the absence or presence of a solvent such as dimethylformamide, preferably at elevated temperature, and optionally in the presence of a base, e.g. sodium hydride or potassium butoxide. The protecting group may be removed from the compound of formula (IX) by reaction with a hydrazine. e.g. hydrazine hydrate, or a primary amine, e.g. methylamine.

Diamines of formula (III) in which $R_5$ is hydrogen and m is 1 may be prepared by reacting an epoxide of formula (X)

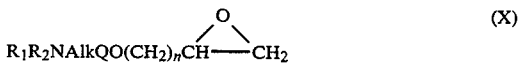
(X)

with an azide, e.g. sodium azide to produce a compound of formula (XI)

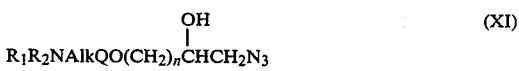
(XI)

which may be reduced to produce a diamine of formula (III) where m is 1. The reaction with the azide may be carried out in a suitable solvent, e.g. aqueous ethanol in the presence of ammonium chloride, preferably at reflux temperature. Reduction of the compound of formula (XI) may be carried out for example, with lithium aluminium hydride in a suitable solvent, e.g. tetrahydrofuran, or catalytically using for example platinum oxide or palladium oxide as catalyst.

Diamines of formula (III) in which $R_5$ is hydrogen and m is 2 may be prepared by reacting the epoxide of formula (X) with a cyanide, e.g. sodium cyanide, to produce a compound of formula (XII)

(XII)

which may be reduced to produce a compound of formula (III) in which m is 2. The reaction with the cyanide may be carried out in a suitable solvent, e.g. aqueous ethanol preferably at reflux temperature. Reduction of the compound of formula (XII) may be carried out, for example with lithium aluminium hydride in a suitable solvent, e.g. tetrahydrofuran. Alternatively the epoxide of formua (X) may be reacted with nitromethane to produce a compound of formula (XIII)

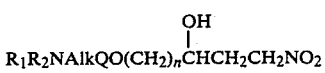

$$R_1R_2NAlkQO(CH_2)_n\overset{|}{C}HCH_2CH_2NO_2 \quad \text{(XIII)}$$

which may be reduced to produce a compound of formula (III) in which m is 2. The reaction with nitromethane may be carried out in a suitable solvent, e.g. dimethylformamide, preferably in the presence of a base, e.g. sodium hydride. Reduction of the compound of formula (XIII) may be carried out for example as described above for reduction of the compound of formula (XII) or using hydrogen in the presence of a catalyst.

The intermediate epoxides of formula (X) may be prepared by alkylation of an appropriate alkalie metal phenolate, e.g. sodium phenolate with a halohydrin (XIV)

The intermediate epoxide of formula (VIII) may be prepared by alkylation of an alkali metal, phthalimide, e.g. potassium phthalimide, with a halohydrin (XV)

Where the product of any of the above processes is a free base and a salt is required, the salt may be formed in a conventional manner. Thus, for example, a generally convenient method of forming the salts is to mix appropriate quantities of the free base and the acid in an appropriate solvent(s) e.g. an alcohol such as ethanol or an ester such as ethyl acetate.

The invention is illustrated but not limited by the following Examples.

In the following Examples and Preparations temperatures are in °C.

T.l.c. refers to thin layer chromatography and this and preparative chromatography were carried out on silica using, unless otherwise stated, one of the following solvent systems.
System A: Dichloromethane:ethanol:0.88 ammonia (50:8:1)
System B: Dichloromethane:ethanol:0.88 ammonia (100:8:1)
System C: Methanol:0.88 ammonia (200:1).

PREPARATION 1

2-[2-Hydroxy-3-[3-(1-piperidinylmethyl)phenoxy]-propyl]-1H-isoindole-1,3-(2H)dione A mixture of 2-(oxiranylmethyl)-1H-isoindole-1,3-(2H)-dione (9.10 g) and 3-(1-piperidinylmethyl)phenol (8.55 g) was heated at 130° C. under nitrogen for 10 minutes. The resulting mixture was dissolved in chloroform (100 ml), washed with 1N sodium hydroxide (2×25 ml), dried (MgSO₄) and evaporated to give the title compound as a gum (17.65 g).

T.l.c. system B, Rf 0.60. (b) Similarly prepared by this procedure from 2-[2-oxiranylethyl]-1H-isoindole-1,3-(2H)dione (19.7 g) and 3-(1-piperidinylmethyl)phenol (17.4 g) except that the crude compound was distilled, was 2-[3-hydroxy-4-[3-(1-piperidinylmethyl)phenoxy]-butyl]-1H-isoindole-1,3-(2H)dione (16.5 g) as an orange oil, b.p. 180° C. (0.05 mm).

N.m.r. (CDCl₃): 2.0–2.35,m,(4H); 2.8,t,(dd),(1H); 3.33,m, (3H); 5.8–6.2,m,(5H); 6.54,s,(2H); 6.95,br,(1H); 7.5–7.7,m,(4H); 7.8–8.2,m,(2H); 8.2–8.7,m,(6H).

PREPARATION 2

1-Amino-3-[3-[(1-piperidinylmethyl)phenoxy]-2-propanol

A solution of 2-[2-hydroxy-3-[3-(1-piperidinylmethyl)phenoxy]propyl]-1H-isoindole-1,3-(2H)dione (17.6 g) and hydrazine hydrate (2.5 g) in ethanol (60 ml) was heated under reflux for 3 h. The resulting mixture was evaporated to a solid residue which was suspended in 1N hydrochloric acid (30 ml) and filtered. The filtrate was basified with an excess of potassium carbonate and extracted with isopropanol (3×40 ml). The isopropanol extracts were dried (Na₂CO₃) and evaporated to a gum which was chromatographed using System A. Crystallisation of the product from n-hexane:ether (20:1) gave the *title compound* as colourless grains (7.7 g), m.p. 74°–76.5°.

(b) Similarly prepared by this procedure from 2-[3-hydroxy4-[3-(1-piperidinylmethyl)phenoxy]butyl]-1H-isoindole 1,3-(2H)dione (16.5 g) and hydrazine hydrate (4.35 g) (except that the crude product was distilled [b.p. 200° (0.06 mm)]) was 4-amino-1-[3-(1-piperidinylmethyl)phenoxy]-2-butanol (7.2 g) as a white solid, m.p. 59°.

(c) Similarly prepared by this procedure from 2-[3-[3-(dimethylaminomethyl)phenoxy]-2-hydroxy-propyl]-1H-isoindole-1,3-(2H)-dione (13.0 g) and hydrazine hydrate (2.1 g) except the crude product was distilled [b.p. 200°, 0.2 mmHg] was 1-amino-3-[3-(dimethylaminomethyl)phenoxy]-2-propanol (3.8 g) as a pale yellow solid.
n.m.r. (CDCl₃): 2.7,t,(1H); ca. 3.2,m,(3H); ca. 6.05,m,(3H); 6.63,s,(2H); 7.15,m,(2H); 7.53,br,m,(2H); 7.78,s,(6H); 7.0–8.3,br,s,(1H).

PREPARATION 3

2-[3-[3-(Dimethylaminomethyl)phenoxy]-2-hydroxypropyl]-1H-isoindole-1,3-(2H)-dione A solution of 2-(oxiranylmethyl)-1H-isoindole-1,3-(2H)-dione (20.3 g) and 3-(dimethylaminomethyl)-phenol (22.3 g) in dimethylformamide (200 ml) with a catalytic amount of sodium hydride (0.2 g) was heated for 6 h at 100° under N₂. The solvent was evaporated to give an oil which was dissolved in chloroform and washed with 2N sodium hydroxide and water. The organic solution was evaporated to give an oil (14 g). A portion of the oil (0.8 g) was distilled to give the *title compound* (0.6 g) as an oil, b.p. 250° (0.08 mmHg).

Found: C, 67.4; H, 6.3; N, 7.8; C₂₀H₂₂N₂O₄ requires: C, 67.8; H, 6.3; N, 7.9%

PREPARATION 4

5-Bromo-1-ethyl-1H-tetrazole

A solution of bromine 3.34 g) in chloroform (2 ml) was added dropwise over 0.25 h to a refluxing solution of 1-ethyl-1H-tetrazole (980 mg) in acetic acid (8 ml) and chloroform (16 ml). The mixture was refluxed for 16 h, was cooled and evaporated to give an oil which was distilled to give the title compound (1.28 g) as an orange oil b.p. 100°–110° (0.08 mm).
n.m.r (CDCl₃): 5.53,q,(2H); 8.40,t,(3H).

PREPARATION 5

1-Amino-4-[3-(1-piperidinylmethyl)phenoxy]-2-butanol (a) 1-[[3-(2-Oxiranylethoxy)phenyl]methyl]piperidine A mixture of 3-(1-piperidinylmethyl)phenol (19.1 g) and flaked potassium hydroxide (6.1 g) in acetonitrile (350 ml) was stirred at room temperature for 16 h. The mixture was warmed to give a uniform solution to which (2-bromoethyl)oxirane (20 g) was added. After 3.5 h at ambient temperature, the solvent was evaporated off and the residue partitioned between diethyl ether (400 ml) and water (100 ml). The organic phase was washed with 1M sodium hydroxide, dried and evaporated at 50° (0.01 mm) to give the *title compound* (18 g) as a light brown oil.

n.m.r. (CDCl$_3$): 2.7–3.4,t+m,(4H); 5.93,t,(2H); 6.6,s,(2H); 6.9,m,(1H); 7.23+7.47,t+dd,(2H); ca. 7.65,m,(4H); ca. 8.0,m,(2H); ca 8.6,m,(6H).

(b)

1-Azido-4-[3-(1-piperidinylmethyl)phenoxy]-2-butanol

A solution of 1-[[3-(2-oxiranylethoxy]phenyl]methyl]piperidine (17 g), sodium azide (5.1 g) and ammonium chloride 2.73 g) in 25% aqueous ethanol (200 ml) was refluxed for 6 h and concentrated to ca. 130 ml. The concentrate was diluted with water (50 ml), saturated with potassium carbonate and extracted with isopropanol. The extract was dried and evaporated to give an oil (20 g) which was chromatographed on silica using dichloromethane:ethanol:ammonia (200:8:1) to give the *title compound* (10.5 g) as a colourless oil.

n.m.r. (CDCl$_3$): 2.75,t,(1H); 3.0–3.3,m,(3H); ca. 5.85,m,(3H); 6.53,s,(2H); 6.58,d,(2H); 7.2,br s,(1H); 7.65,m,(4H); 8.05,m,(2H); ca. 8.5,m,(6H).

(c)

1-Amino-4-[3-(1-piperidinylmethyl)phenoxy]-2-butanol

A solution of 1-azido-4[3-(1-piperidinylmethyl)phenoxy]-2-butanol (10 g) in dry tetrahydrofuran (100 ml) was added dropwise to a stirred suspension of lithium aluminium hydride (4 g) in tetrahydrofuran (200 ml) under nitrogen. The resulting mixture was stirred at room temperature for 1 h and quenched with water (4 ml), followed by 15% sodium hydroxide (4 ml) and water (12 ml). The mixture was then filtered and the residue washed with tetrahydrofuran (50 ml). The combined filtrate was evaporated to give the *title compound* (7.5 1 g) as a pale pink oil.

n.m.r. (CDCl$_3$): 2.78,t,(1H); 3.0–3.32,m,(3H); 5.88,t,(2H); 6.22,m,(1H); 6.58,s,(2H); 7.0–7.5,ABX,(2H), 7.6,m,(4H), 7.73,brs,(3H); 8.1,m,(2H); ca. 8.5,m,(6H).

EXAMPLE 1

1-[(1-Methyl-1H-tetrazol-5-yl)amino]-3-[3-(1-piperidinylmethyl)phenoxy]-2-propanol A solution of 1-amino-3-[3-(1-piperidinylmethyl)phenoxy]-2-propanol (1.19 g) and 5-bromo-1-methyl-1H-tetrazole (0.735 g) in absolute ethanol (6 ml) was heated in an autoclave at 125° for 18 h. The mixture was cooled, evaporated, saturated with sodium carbonate solution (30 ml) and ethyl acetate (30 ml) added. The mixture was stirred for 15 min. and filtered to give a white solid (830 mg) which was recrystallised from ethyl acetate (20 ml) to give the *title compound* (0.58 g) as white micro-crystals, m.p. 156°–7°.

Analysis Found: C, 58.73; H, 7.60; N, 24.24; C$_{17}$H$_{26}$N$_6$O$_2$ Requires: C, 58.94; H, 7.57; N, 24.26%.

EXAMPLE 2

1-[(1-Ethyl-1H-tetrazol-5-yl)amino]-3-[3-(1-piperidinylmethyl)phenoxy]-2-propanol A mixture of 1-amino-3-[(1-piperidinylmethyl)-phenoxy]-2-propanol (1.06 g) and 5-bromo-1-ethyl-1H-tetrazole (0.7 g) in water (20 ml) was stirred at reflux for 18 h. Excess potassium carbonate was added and the mixture was extracted with ethyl acetate. The extract was washed with brine, dried (MgSO$_4$) and evaporated to give an oil which was crystallised from methyl acetate-light petroleum (b.p. 60°–80°) to give the *title compound* (530 mg) as white microcrystals, m.p. 111°–13°.

Found: C, 59.9; H, 7.8; N, 23.0; C$_{18}$H$_{28}$N$_6$O$_2$ requires: C, 60.0; H, 7.8; N, 23.3%.

EXAMPLE 3

1-[(1-Methyl-1H-tetrazol-5-yl)amino]-4-[3-(1-piperidinylmethyl)phenoxy]-2-butanol A solution of 1-amino-4-[3-(1-piperidinylmethyl)-phenoxy]-2-butanol (1.39 g) and 5-bromo-1-methyl-1H-tetrazole (0.82 g) in absolute ethanol (10 ml) was heated in an autoclave at 125° for 18 h. The solution was evaporated and the residue dissolved in 1M hydrochloric acid (25 ml). The acidic solution was washed with ethyl acetate, basified with excess sodium carbonate and extracted with ethyl acetate. The extract was dried and evaporated to leave a solid which was triturated with dry diethyl ether to give a white solid (1.0 g). This solid was recrystallised from methyl acetate-light petroleum (b.p. 60°–80°) to give the *title compound* (0.6 g) as white crystals, m.p. 138°–9°.

Found: C, 59.8; H, 7.9; N, 23.2; C$_{18}$H$_{28}$N$_6$O$_2$ requires: C, 60.0; H, 7.8; N, 23.3%.

Examples of Pharmaceutical Compositions

| 1. Tablets | mg/tablet |
|---|---|
| Active ingredient | 5.0 to 25.0 |
| Lactose | 131.5 to 111.5 |
| Pregelatinised maize starch | 7.5 |
| Sodium starch glycollate | 4.5 |
| Magnesium stearate | 1.5 |
| Compression weight | 150.0 |

The active ingredient is sieved through a 250 μm sieve and blended with the lactose and pregelatinised maize starch. This mix is granulated by the addition of water. The granules are dried, screened and blended with the sodium starch glycollate and magnesium stearate. The lubricated granules are compressed into tablets using 8.0 mm diameter punches.

| 2. Injections | % w/v |
|---|---|
| Active ingredient | 0.5 |
| Water for injection B.P. to | 100.0 |

Sodium chloride may be added to adjust the tonicity of the solution and the pH may be adjusted to that of maximum stability using dilute acid or alkali or by the addition of suitable buffer salts.

The solution is prepared, clarified and filled into appropriate sized ampoules sealed by fusion of the glass. The injection is sterilised by heating in an autoclave

We claim:
1. A compound of formula (I)

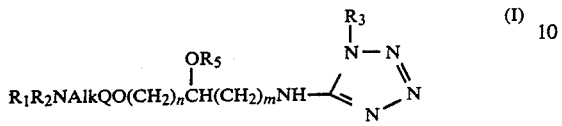

or a physiologically acceptable salt or hydrate thereof, in which $R_1$ represents hydrogen, $C_{1-14}$ alkyl, $C_{3-8}$ cycloalkyl, $C_{3-6}$ alkenyl, $C_{3-6}$ alkynyl, ar $C_{1-6}$ alkyl wherein the aryl group is phenyl or phenyl substituted by one or more $C_{1-3}$ alkyl or alkoxy groups or halogen atoms; trifluoro $C_{1-6}$ alkyl, heteroaralkyl, wherein the heteroaryl group is thienyl, pyrrolyl, pyridyl, furyl or thiazolyl, which is unsubstituted or substituted by $C_{1-3}$ alkyl, $C_{1-3}$ alkoxy, hydroxy $C_{1-6}$ alkyl, amino $C_{1-6}$ alkyl, $C_{1-6}$ alkylamino $C_{1-6}$ alkyl, di $C_{1-6}$ alkylamino $C_{1-6}$ alkyl or halogen, the alkyl portion of the heteroaralkyl group is a straight or branched $C_{1-4}$ alkyl chain, and the heteroaryl ring is linked to the alkyl portion through a carbon atom; or $C_{1-6}$ alkyl substituted by $C_{3-8}$ cycloalkyl, hydroxy, $C_{1-6}$ alkoxy, amino, $C_{1-6}$ alkylamino or di $C_{1-6}$ alkylamino;

$R_2$ represents hydrogen or a $C_{1-4}$ alkyl group;

or $R_1$ and $R_2$ together with the nitrogen atom to which they are attached form piperidino, morpholino, 4-methyl piperidino, pyrrolidino, hexamethyleneimino or tetrahydropyridino;

Alk represents a straight or branched alkylene chain of 1 to 3 carbon atoms;

Q represents a benzene ring in which incorporation into the rest of the molecule is through bonds at the 1- and 3- or 1- and 4-positions;

$R_5$ represents hydrogen or acyl;

n and m, which may be the same or different, are each 1 or 2; and $R_3$ represents hydrogen, $C_{1-6}$ alkyl, $C_{3-6}$ alkenyl, ar $C_{1-6}$ alkyl, wherein the aryl group is phenyl or phenyl substituted by one or more $C_{1-3}$ alkyl or alkoxy groups or halogen atoms; hydroxy $C_{2-6}$ alkyl, $C_{1-6}$ alkoxy $C_{2-6}$ alkyl or $C_{1-4}$ alkanoyloxy $C_{2-6}$ alkyl.

2. A compound as claimed in claim 1 in which
$R_1$ represents $C_{1-8}$ alkyl, $C_{1-4}$ alkyl substituted by a trifluoromethyl group, $C_{2-4}$ alkyl substituted by hydroxy or a di $C_{1-3}$ alkylamino group, $C_{5-7}$ cycloalkyl, $C_{3-5}$ alkenyl, phenyl $C_{1-3}$ alkyl, or a heteroaryl $C_{1-3}$ alkyl group where the heteroaryl ring is furyl, thienyl, pyrrolyl, or pyridyl;

$R_2$ represents hydrogen or methyl; or $R_1R_2N$ represents piperidino, morpholino, 4-methyl piperidino, pyrrolidino, hexamethyleneimino or tetrahydropyridino;

Alk represents methylene;

$R_3$ represents hydrogen, $C_{1-6}$ alkyl or hydroxy $C_{2-4}$ alkyl;

Q represents a benzene ring incorporated into the rest of the molecule through bonds at the 1- and 3-positions;

$R_5$ represents hydrogen or $C_{1-6}$ alkanoyl; and n and m both represent 1, or one of n and m represents 2.

3. A compound as claimed in claim 1 wherein $R_5$ represents hydrogen or a $C_{1-4}$ alkanoyl group.

4. A compound as claimed in claim 1 of formula (II)

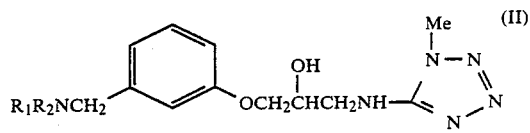

in which $R_1R_2N$ is dimethylamino, pyrrolidino, piperidino or hexamethylenimino.

5. 1-[(1-Methyl-1H-tetrazol-5-yl)amino]-3-[3-(1-piperidinylmethyl)phenoxy]-2-propanol; and physiologically acceptable salts thereof.

6. A pharmaceutical composition for the treatment of conditions mediated through histamine $H_2$-receptors which comprises an effective amount to relieve said condition of a compound as claimed in claim 1 together with at least one inert pharmaceutically acceptable carrier or diluent.

7. A method of treating a condition mediated through histamine $H_2$-receptors which comprises administering to a patient an effective amount of a compound as claimed in claim 1 to relieve said condition.

* * * * *